US006566388B2

(12) United States Patent
Mizutani et al.

(10) Patent No.: US 6,566,388 B2
(45) Date of Patent: *May 20, 2003

(54) EMULSIFIABLE COMPOSITION FOR THE CONTROL OF INSECTS

(75) Inventors: Takaaki Mizutani, Nishinomiya (JP); Michihiko Ikeda, Minamikawachi-gun (JP); Hiroshi Kodama, Kawachinagano (JP); Masakazu Shibayama, Takatsuki (JP)

(73) Assignee: Rhone-Poulenc Agrochimie, Lyons (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/849,051

(22) PCT Filed: Nov. 29, 1995

(86) PCT No.: PCT/EP95/04686

§ 371 (c)(1), (2), (4) Date: Aug. 22, 1997

(87) PCT Pub. No.: WO96/16544

PCT Pub. Date: Jun. 6, 1996

(65) Prior Publication Data

US 2002/0042440 A1 Apr. 11, 2002

(30) Foreign Application Priority Data

Nov. 30, 1994 (JP) .............................................. 6-321644

(51) Int. Cl.$^7$ ........................ A01N 43/56; A01N 25/02; A01N 25/22

(52) U.S. Cl. ........................... 514/407; 14/404; 14/406; 14/772; 14/875; 14/937; 14/970; 14/971; 14/975; 424/DIG. 11

(58) Field of Search ................................. 514/406, 407, 514/937, 875, 970, 971, 404, 772, 975; 424/DIG. 11

(56) References Cited

U.S. PATENT DOCUMENTS

| | | | |
|---|---|---|---|
| 5,232,940 A | | 8/1993 | Hatton et al. ................ 514/407 |
| 5,328,693 A | | 7/1994 | Horstmann et al. ......... 424/405 |
| 6,010,710 A | * | 1/2000 | Etchegaray .................. 424/405 |
| 6,066,660 A | * | 5/2000 | Mizutani et al. ............ 514/359 |
| 6,096,329 A | * | 8/2000 | Jeannin ....................... 424/405 |

FOREIGN PATENT DOCUMENTS

| | | |
|---|---|---|
| EP | 0295117 | 12/1988 |
| EP | 0418016 | 3/1991 |
| EP | 0453915 | 10/1991 |
| GB | 1473105 | 5/1977 |
| GB | 2077104 | 12/1981 |
| WO | 91/08665 | 6/1991 |
| WO | 93/06089 | 4/1993 |
| WO | 94/21606 | 9/1994 |

OTHER PUBLICATIONS

Chemical Abstract 117 (13) : 126422, Sep. 1992.*
*The Condensed Chemical Dictionary*, tenth edition, ed. Gessner G. Hawley, Van Nostrand Reinhold Company Inc., New York, New York, p. 690 (1981).

* cited by examiner

Primary Examiner—John Pak
(74) Attorney, Agent, or Firm—Burns, Doane, Swecker & Mathis, L.L.P.

(57) ABSTRACT

An emulsifiable composition for the control of insects, especially of termites, comprising a 1-substituted phenyl-3-cyanopyrazole, a weakly polar solvent and an emulsifying agent, optionally comprising further additives or solvents. These compositions avoid the formation of crystals.

31 Claims, No Drawings

EMULSIFIABLE COMPOSITION FOR THE CONTROL OF INSECTS

This application is a continuation (CPA) of U.S. patent application Ser. No. 08/849,051, filed on Aug. 22, 1997, which was a national stage filing under 35 U.S.C. §371 of International Patent Application No. PCT/EP95/04686, filed Nov. 29, 1995 and designating the United States, which claims the priority under 35 U.S.C. §119 of Japanese Patent Application No. 94/32 1644, filed Nov. 30, 1994, both hereby expressly incorporated by reference, which International Application was published by the International Bureau on Jun. 6, 1996, in English, as WO 96/16544.

The present invention relates to an emulsifiable composition for the control of insects and a method of use thereof. The emulsifiable compositions of the present invention derive from 1-substituted phenyl pyrazoles insecticides and they do not favor the formation of crystals.

The 1-substituted phenyl pyrazoles insecticides can be liable to generate some crystallizations within the compositions during storage or use. When using such compounds for various applications, there may be problems of crystallization or recrystallization which prohibit a proper and easy application. This may happen in a quite different number of practical applications such as spray applications through a nozzle which may be clogged; dilution in a tank whereby the active ingredient may thus crystallize and fall at the bottom of the tank; application to animal's hair whereby the quality of the hair may be damaged by deposit of crystals thereon. For companion animals a most important requirement is to have a high quality hair, which is nice and pleasant when touching or petting.

Furthermore it is frequent that specialists in the control of insects, especially of termites, prepare a diluted pesticidal liquid the day before the application and utilize the remaining liquid the day after. These liquids, since they contain crystalline active ingredients, are poorly emulsified and are liable to crystallize in several hours after preparation of spraying emulsion, resulting in a great volume of liquid of no use or causing the clogging of pump nozzles employed for foam application.

In the particular situation of methods of control of insects, especially of termites, these methods may generally be divided into two main groups. On one side is the wood treatment according to which wooden parts of a house are subjected to pesticidal treatment and the other is called the soil treatment according to which a liquid pesticide is sprayed onto the underfloor area of a house. The application of a flowable formulation in which the active ingredient is suspended in water is becoming predominant, considering the health of the workers on an application within the limited space under the floor. However such dilution of water has the tendency to generate crystals. The conventional flowable formulation are not satisfactory.

Japanese Patent Publication No. 2-7282 has proposed to prevent the crystallization of some active ingredients which are not 1-substituted phenyl pyrazoles insecticides. Japanese Patent Application No. 50-69230 has described a liquid herbicidal composition containing as active ingredients thereof a dinitroaniline herbicide and a N-allyl-N'-alkoxy urea herbicide. It discloses also the use of an emulsifying agent and a solvent consisting of an alicyclic ketone in order to give to the composition the physical stability under the conditions of transportation, storage and end use.

An object of the present invention is to provide improved emulsifiable compositions which reduce the odor of the solvent(s) and/or prevent the crystallization of the 1-substituted phenyl pyrazoles insecticides upon dilution and/or are generally superior to the conventional flowable formulations.

The emulsifiable compositions of the present invention contain:
   an insecticidally active ingredient which is a compound of formula (I), and
   one, or more, weakly polar solvent, and
   an emulsifying agent, and optionally
   one, or more, further solvent(s).

Formula (I) for compounds used as active ingredient in the invention is

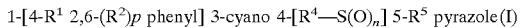

1-[4-$R^1$ 2,6-($R^2$)$p$ phenyl] 3-cyano 4-[$R^4$—S(O)$_n$] 5-$R^5$ pyrazole (I)

wherein:
   $R^1$ is halogen, lower haloalkyl, lower haloalkoxy or $SF_5$ (lower being an integer from 1 to 4, preferably one),
   $R^2$ is halogen, the various $R^2$ being identical or different,
   $R^4$ is halogen, lower alkyl or haloalkyl,
   $R^5$ is halogen, lower alkyl or amino,
   n is 0 or 1 or 2; p is 0 or 1 or 2, preferably 2.

Halo before the name of a radical means that this radical may be substituted by one or more halogen atoms.

A preferred compound of formula (I) is compound 5-amino-3-cyano-1-(2,6-dichloro-4-trifluoromethylphenyl)-4-trifluoromethylsulfinylpyrazole, hereinafter referred to as compound (A).

The compositions of the invention are useful for the treatment of many insects, especially termites, fleas, or arachnids such as ticks, and more generally insects on dogs or cats and other companion animals, as well as other insects as cited in European patent application 295117 which is herein incorporated by reference.

The compounds of formula (I) employed in the emulsifiable composition for the control of insects, especially of termites, of the present invention are known and described in the European patent application No. 295117 as well as in international patent applications WO 93/6089 and 94/21606. They are effective for the control of arthropods, plant nematodes, protozoan pests, insects, especially of termites, farm pests and the like.

Weakly polar solvents which may be used in the invention are generally those which have a dipolar moment positive, preferably higher than 1 (the unit is the debye) and a solubility in water (at 20° C.) of less than 10%. These weakly polar solvent(s) are preferably selected among the cyclic amides and the glycolic ether solvents.

Examples of cyclic amides which may be used are N-octyl-2-pyrrolidone, N-dodecyl-2-pyrrolidone and N-dodecyl-caprolactam.

Examples of weakly polar solvent(s) of the glycolic ether type are ethylene glycol monophenyl ether, ethylene glycol monohexyl ether, ethylene glycol mono-2-ethylhexyl ether, ethylene glycol dibutyl ether, diethylene glycol dibutyl ether, propylene glycol monophenyl ether, dipropylene glycol monopropyl ether, ethylene glycol monobenzyl ether and the like. Preferred glycol solvent is diethylene glycol mono-2-ethylhexyl ether.

Emulsifing agents which may be used are preferably one or more of those selected from nonionic or anionic emulsifying agents. Examples of nonionic emulsifying agents which may be mentioned include: polyoxyalkylether, polyoxyethylenealkylphenylether, polyoxyethylenealkylether, polyethyleneglycol fatty ester, sorbitan fatty ester, polyoxyethylene sorbitan fatty ester, polyoxyethylenesorbit fatty ester, polyoxyethylenepolyoxypropylenealkylether, polyoxyethylene (castor oil) ether. Examples of anionic emulsifying agents which may be mentioned include alkyl sulphates, polyxyethylenealkylether sulphates, sulfosuccinates, taurine derivatives, sarcosine derivatives, alkylbenzenesulfonates and the like. Preferred emulsifying agents are mixtures comprising of polyoxyethylene styrylphenylether and calcium alkylbenzenesulfonate (emulsifying agent a), and mixtures comprising of polyoxyethylene (castor oil) ether and calcium alkylbenzenesulfonate (emulsifying agent b).

Aromatic solvents may be used in the compositions of the present invention, generally to improve the solubility and/or the penetrability of the active ingredient. These aromatic solvent(s) are preferably selected from those being in liquid state at normal temperature (that is to say liquid at room temperature or at some temperature below 30° C.) and having a boiling point of at least 200° C. They may be more particularly selected from petroleum fraction, catalytic cracked oil fraction or synthetic oil and the like. Examples which may be mentioned include: mono- or polyalkylbenzenes such as alkylbenzene or trimethylbenzene; naphthalenes such as methylnaphthalene, dimethylnaphthalene, dimethylmonopropylnaphthalene, dimethyldipropylnaphthalene or phenylxylylnaphthalene; alkyldiphenylalkanes such as 1-phenyl-1-xylylethane or alkyldiphenylethane; indene derivatives; dibenzylethers; diester phthalates and the like. 1-phenyl-1-xylylethane, dibenzyl ethers, dimethyl monopropyl naphthalene, dimethly dipropyl naphthalene are preferred.

If necessary, the composition of the present invention may contain a more polar solvent. Polar solvents which are not weakly polar solvents are generally those which have a dipolar moment positive, preferably higher than 1 (the unit is the debye) while having a solubility in water higher than 10%. Such polar solvents include cyclic amides or lactones such as N-methyl-2-pyrrolidone, N-cyclohexyl-2-pyrrolidone, caprolactone, butyrolactone; and glycol ethers such as tripropyleneglycolmonomethylether, diethyleneglycoldimethylether.

Even though the proportions of each component of the compositions of the invention may vary in a broad range of values, the advantageous compositions which are further preferred are those which comprise (the proportions are indicated as percentage by weight, which are the same as weight parts per 100 weight parts of the compositions):

1 to 10% of insecticidally active ingredient(s), and/or 3 to 90% of weakly polar solvent(s), more preferably 5 to 30%, and/or 5 to 40% of emulsifying agent(s), and/or optionally 0 to 90% of a further aromatic solvent or solvent(s); the proportion of this (these) solvent(s) in the composition of the invention is advantageously more than 50%; and/or optionally 0 to 20% of a more polar solvent(s) as herein before defined.

Emulsifiable compositions of the present invention may also contain other additives according the general knowledge of the art of agrochemical formulation making. For certain applications, especially for termite control and/or houses underfloor treatment, some specific additives may be added such as foaming agents or foam stabilizer.

Emulsifiable compositions of the present invention may be prepared by any of conventional procedures suitable for emulsifiable concentrates.

The invention relates also to a method of control of termites whereby an effective amount of a composition as hereinbefore described is applied to the locus which is infested or expected to be infested by said pests. Applications can be made according any suitable means, such as spraying, coating, impregnating. The compositions of the present invention, when used against termites, may be applied not only to treat the surface or the interior of soil or under-floor soil for protecting wood such as trees, fences, and railroad ties, or buildings such as houses, warehouses, and industrial plants, but also in timber products such as plywood and furniture, wood products such as particle boards and half boards, and vinyl products such as coated wires and sheets. The compositions of the inventions may be also used in all other kind of applications, including agrochemical applications to crop area and veterinary uses.

The invention further relates to a method of control of fleas or ticks or insects from animals such as dogs and cats whereby an effective amount of a composition as hereinbefore described is applied to the animal which is infested or expected to be infested by said pests, the applied dosis of the active ingredients being preferably 0.1 to 100 mg, preferably at 2 to 20 mg per kilogram of body weight of the animal.

When the compositions for soil treatment of the present invention are used for insect control, for example for termite control, especially for soil treatment and/or for treating under-floor soil, the quantity of the effective ingredient may be within a range between 0.01 mg and 15 mg, preferably between 0.1 mg and 5 mg per square meter.

The present invention is illustrated by the following examples, comparative examples and experimental examples, but is not limited to the details thereof. Unless otherwise specified, parts are by weight.

EXAMPLE 1

5 part of the compound (A), 15 parts of N-octyl-2-pyrrolidone, 10 parts of emulsifying agent a (Solpol 355X available from Toho Kagaku Kogyo K.K.) and 70 parts of 1-phenyl-1-xylylethane were homogeneously dissolved to obtain an emulsifiable composition of the present invention.

EXAMPLE 2 to 29

In each of these examples, an emusifiable composition of the present invention was prepared in a similar manner to Example 1 according to the corresponding formulation shown in the Table 1 for examples 1 to 15, and according to Table 2 for examples 16 to 29.

COMPARATIVE EXAMPLE 1

2 parts of the compound (A), 5 parts of N-methyl-2-pyrrolidone, 15 parts of the emulsifying a agent and 78 parts of 1-phenyl-1-xylylethane were mixed and dissolved to obtain an emulsifiable composition.

COMPARATIVE EXAMPLE 2

2 parts of the compound (A), 5 parts of propylene glycol, 5 parts of dispersing agent (polyoxyethylene styryl phenyl ether; Penerol SP2440, available from Matsumoto Yushi Seiyaku k.k.), 1 part of wetting agent (sodium dioctylsulfosuccinate), 0.25 part of xanthane gum, 0.5 part of silicon antifoaming agent and 86.25 parts of water were homogeneously mixed to obtain a suspension composition.

PHYSICAL EFFICACY: EXPERIMENTAL EXAMPLE 1

Crystallization Test in Diluted Liquid

To a 100 milliliter beaker, 100 ml of 3° hard water was introduced, 2.5 g of an emulsifiable composition prepared according to each of the above examples and comparative examples was added thereto, then stirred and mixed well. After being left to stand at 5° C. for 24 hours, the obtained diluted liquid was passed through a sieve of 45 microns opening, then the amount of crystal remaining on the sieve was evaluated by visual observation.

No crystal or crystallization was observed for any of the examples 1 to 29. On the contrary, large amounts of crystals and crystallisation was observed for Comparative example 1.

BIOLOGICAL EFFICACY: EXPERIMENTAL EXAMPLE 2

Termites Controlling Test

An experimental system comprising two glass cylindrical tubes (inner diameter about 5 cm, height about 12 cm) which were connected with a glass tube (inner diameter about 1.5 cm, height about 10 cm) at the distance of about 2 cm from the bottoms of the cylindrical tubes was used. Into one of the glass cylindrical tube, about 60 g of a non-treated soil whose moisture content had been controlled to be 25% was introduced and into another tube, about 0.29 g of a filter paper (diameter 5.5 mm) was introduced.

2.4 g of the non-treated soil passed through 200 mesh sieve (75 microns size of opening) and dried at 60° C.; they were mixed with 0.6 g of the liquid to be tested (compositions of Example 1 and comparative example 2) diluted with water and kept at room temperature for 3 weeks. Then the resultant mixture was introduced into the center region of the glass tube and then the system was assembled.

220 termites (*Coptotermes formosanus*; 200 workers and 20 soldiers) were introduced in the glass cylindrical tube containing the non-treated soil. The system was then allowed to stand at 28° C. and the humidity was 70% or more. After 21 days from the introduction of the insects, the boring distance (cm) was determined. The results are shown in Table 3.

TABLE 1

| EXAMPLE N° | 1 | 2 | 3 | 4 | 5 |
|---|---|---|---|---|---|
| Compound (A) | 5.0 | 5.0 | 5.0 | 5.0 | 1.0 |
| N-Octyl-2-pyrrolidone | 15.0 | | | 10.0 | 3.0 |
| N-Dodecyl-2-pyrrolidone | | 15.0 | | | |
| N-dodecylcaprolactam | | | 15.0 | | |
| N-methyl-2-pyrrolidone | | | | 2.0 | |
| Solpol 355 | 10.0 | 10.0 | 10.0 | 10.0 | 10.0 |
| 1-phenyl-1-xylyethane | 70.0 | 70.0 | 70.0 | 73.0 | 86.0 |
| TOTAL | 100.0 | 100.0 | 100.0 | 100.0 | 100.0 |

| EXAMPLE N° | 6 | 7 | 8 | 9 |
|---|---|---|---|---|
| Compound (A) | 3.0 | 10.0 | 10.0 | 5.0 |
| N-Octyl-2-pyrrolidone | 10.0 | 30.0 | 20.0 | 15.0 |
| N-methyl-2-pyrrolidone | | | 5.0 | |
| Solpol 355 | 10.0 | 10.0 | 10.0 | 10.0 |
| 1-phenyl-1-xylyethane | 77.0 | 50.0 | 55.0 | |
| Dibenzylether | | | | 70.0 |
| TOTAL | 100.0 | 100.0 | 100.0 | 100.0 |

| EXAMPLE N° | 10 | 11 | 12 | 13 |
|---|---|---|---|---|
| Compound (A) | 5.0 | 5.0 | 5.0 | 5.0 |
| N-Octyl-2-pyrrolidone | 15.0 | 15.0 | 15.0 | 15.0 |
| Solpol 355 | 10.0 | 10.0 | 10.0 | 10.0 |
| Dimethylmonopropylnaphthalene | 70.0 | | | |
| Dimethyldipropylnaphthalene | | 70.0 | | 20.0 |
| Diethyleneglycol mono-(2-ethylhexyl)ether | | | 70.0 | 50.0 |
| TOTAL | 100.0 | 100.0 | 100.0 | 100.0 |

| EXAMPLE N° | 14 | 15 |
|---|---|---|
| Compound (A) | 5.0 | 5.0 |
| N-Octyl-2-pyrrolidone | 10.0 | 10.0 |
| N-methyl-2-pyrrolidone | 2.0 | 2.0 |
| Solpol 355 | 10.0 | 10.0 |
| Dimethyldipropylnaphthalene | 73.0 | 23.0 |
| Diethyleneglycole mono(2-ethylhexyl)ether | | 50.0 |
| TOTAL | 100.0 | 100.0 |

| EXAMPLE N° | 16 | 17 | 18 | 19 | 20 | 21 | 22 | 23 |
|---|---|---|---|---|---|---|---|---|
| Compound (A) | 2.0 | 2.0 | 2.0 | 2.0 | 2.0 | 10.0 | 1.0 | 2.0 |
| Ethyleneglycol mono(2-ethylhexyl) ether | 73.0 | 73.0 | 73.0 | 73.0 | | | | |
| Ethyleneglycol monophenyl ether | | | | | 73.0 | 40.0 | 84.0 | 43.0 |
| Ethyleneglycol monobenzyl ether | | | | | | | | 30.0 |
| emulsifying agent b | 20.0 | 20.0 | 20.0 | 20.0 | 20.0 | 40.0 | 15.0 | 20.0 |
| N-methyl-2-pyrrolidone | | | | | | 10.0 | | 5.0 |
| N-cyclohexyl-2-pyrrolidone | 5.0 | | | | | | | |
| gamma butyrolactone | | 5.0 | | | | | | |
| epsilonn caprolactone | | | 5.0 | | | | | |
| tripropylene glycol mono-methylether | | | | 5.0 | | | | |
| diethylene glycol dimethylether | | | | | 5.0 | | | |
| TOTAL | 100.0 | 100.0 | 100.0 | 100.0 | 100.0 | 100.0 | 100.0 | 100.0 |

| EXAMPLE N° | 24 | 25 | 26 | 27 | 28 | 29 |
|---|---|---|---|---|---|---|
| Compound (A) | 2.0 | 2.0 | 2.0 | 2.0 | 1.0 | 2.0 |
| N-octyl-2-pyrrolidone | | | | | 3.0 | 2.0 |
| Ethyleneglycol mono(2-ethylhexyl) ether | | | | | | 20.0 |
| Ethyleneglycol monophenyl ether | 70.0 | | | | | 15.0 |
| Ethyleneglycol monobenzyl ether | | 70.0 | | | | |
| dipropylene glycol mono-propylether | | | 70.0 | | | |
| diethylene glycol dibutylether | | | | 70.0 | | |
| emulsifying agent a | | | | | 10.0 | |
| emulsifying agent b | 23.0 | 23.0 | 23.0 | 20.0 | | 20.0 |
| N-methyl-2-pyrrolidone | 5.0 | 5.0 | 5.0 | | | |

TABLE 1-continued

| | | | | | | |
|---|---|---|---|---|---|---|
| Diisopropylnaphthalene | | | | | 86.0 | 41.0 |
| TOTAL | 100.0 | 100.0 | 100.0 | 100.0 | 100.0 | 100.0 |

TABLE 3

| | Concentration % | Boring distance (cm) |
|---|---|---|
| Experimentation Example 1 | 0.1 | 0.3 |
| | 0.05 | 0.5 |
| | 0.025 | 0.6 |
| Comparative Example 2 | 0.1 | pass-through |
| | 0.05 | pass-through |
| | 0.025 | pass-through |

What is claimed is:

1. A method for controlling termites at a locus infested thereby or expected to be infested thereby, said method comprising applying to said locus a termiticidally effective amount of an emulsifiable composition consisting essentially of:
   (a) a termiticidally effective amount of a compound having the formula:

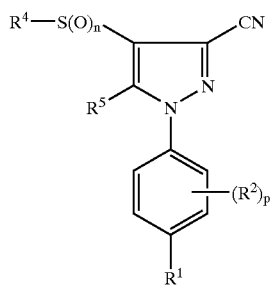

(I)

wherein:
   $R^1$ is halogen, $C_1$–$C_4$ haloalkyl, $C_1$–$C_4$ haloalkoxy or $SF_5$;
   $R^2$ is halogen, the various $R^2$ being the same or different and being in the 2-, the 6- or the 2,6-positions;
   $R^4$ is halogen, $C_1$–$C_4$ alkyl or $C_1$–$C_4$ haloalkyl;
   $R^5$ is halogen, $C_1$–$C_4$ alkyl or amino;
   n is 0, 1 or 2; and
   p is 0, 1, or 2;
   in an amount of from 1 to 10% by weight of the total weight of the composition;
   (b) a weakly polar solvent having a positive dipole moment greater than 1 and a solubility in water of less than 10%, in an amount of from 3 to 90% by weight of the total weight of the composition, the weakly polar solvent consisting of one or more members selected from the group consisting of N-octyl-2-pyrrolidone, N-dodecyl-2-pyrrolidone, N-dodecyl-caprolactam and a glycolic ether; and
   (c) an emulsifying agent selected from a mixture of polyoxyethylene styryl phenyl ether and calcium alkylbenzenesulfonate or a mixture of polyoxyethylene (castor oil) ether and calcium alkylbenzenesulfonate, in an amount of from 5 to 40% by weight of the total weight of the composition;
   wherein said composition is capable of dilution with water without formation of crystals.

2. A method according to claim 1, wherein $R^1$ is halogen, halomethyl, halomethoxy or $SF_5$; $R^4$ is halogen, methyl or halomethyl; $R^5$ is halogen, methyl or amino; and p is 2.

3. A method according to claim 1, wherein the compound of formula (I) is 5-amino-3-cyano-1-(2,6-dichloro-4-trifluoromethylphenyl)-4-trifluoromethylsulfinylpyrazole.

4. A method according to claim 1, wherein the glycolic ether consists of one or more members selected from the group consisting of ethylene glycol monophenyl ether, ethylene glycol monohexyl ether, ethylene glycol mono-2-ethylhexyl ether, ethylene glycol dibutyl ether, diethylene glycol dibutyl ether, propylene glycol monophenyl ether, dipropylene glycol monopropyl ether and ethylene glycol monobenzyl ether.

5. A method according to claim 1, wherein the glycolic ether is diethylene glycol mono-2-ethylhexyl ether.

6. A method according to claim 1, wherein the amount of weakly polar solvent is from 5 to 30% by weight of the total weight of the composition.

7. A method according to claim 1, wherein the amount of compound of formula (I) applied is from 0.01 to 15 mg/m².

8. A method according to claim 1, wherein the amount of compound of formula (I) applied is from 0.1 to 5 mg/m².

9. A method for controlling termites at a locus infested thereby or expected to be infested thereby, said method comprising applying to said locus a termiticidally effective amount of an emulsifiable composition consisting essentially of:
   (a) a termiticidally effective amount of a compound having the formula:

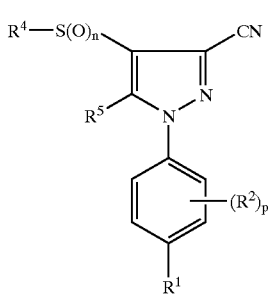

(I)

wherein:
   $R^1$ is halogen, $C_1$–$C_4$ haloalkyl, $C_1$–$C_4$ haloalkoxy or $SF_5$;
   $R^2$ is halogen, the various $R^2$ being the same or different and being in the 2-, the 6- or the 2,6-positions;
   $R^4$ is halogen, $C_1$–$C_4$ alkyl or $C_1$–$C_4$ haloalkyl;
   $R^5$ is halogen, $C_1$–$C_4$ alkyl or amino;
   n is 0, 1 or 2; and
   p is 0, 1, or 2;
   in an amount of from 1 to 10% by weight of the total weight of the composition;
   (b) a weakly polar solvent having a positive dipole moment greater than 1 and a solubility in water of less than 10%, in an amount of from 3 to 90% by weight of the total weight of the composition, the weakly polar solvent consisting of one or more members selected from the group consisting of N-octyl-2-pyrrolidone, N-dodecyl-2-pyrrolidone, N-dodecyl-caprolactam and a glycolic ether;
   (c) an emulsifying agent selected from a mixture of polyoxyethylene styryl phenyl ether and calcium alkylbenzenesulfonate or a mixture of polyoxyethylene (castor oil) ether and calcium alkylbenzenesulfonate, in an amount of from 5 to 40% by weight of the total weight of the composition; and (d) an aromatic solvent which is in liquid state at a temperature below 30° C. or which has a boiling point of at least 200° C., in an amount of up to 90% by weight of the total weight of the composition;

wherein said composition is capable of dilution with water without formation of crystals.

10. A method according to claim 9, wherein $R^1$ is halogen, halomethyl, halomethoxy or $SF_5$; $R^4$ is halogen, methyl or halomethyl; $R^5$ is halogen, methyl or amino; and p is 2.

11. A method according to claim 9, wherein the compound of formula (I) is 5-amino-3-cyano-1-(2,6-dichloro-4-trifluoromethylphenyl)-4-trifluoromethylsulfinylpyrazole.

12. A method according to claim 9, wherein the weakly polar solvent is diethylene glycol mono-2-ethylhexyl ether.

13. A method according to claim 9, wherein the amount of weakly polar solvent is from 5 to 30% by weight of the total weight of the composition.

14. A method according to claim 9, wherein the amount of aromatic solvent is more than 50% by weight of the total weight of the composition.

15. A method according to claim 9, wherein the amount of compound of formula (I) applied is from 0.01 to 15 mg/m².

16. A method according to claim 9, wherein the amount of compound of formula (I) applied is from 0.1 to 5 mg/m².

17. A method for controlling termites at a locus infested thereby or expected to be infested thereby, said method comprising applying to said locus a termiticidally effective amount of an emulsifiable composition consisting essentially of:

(a) a termiticidally effective amount of a compound having the formula:

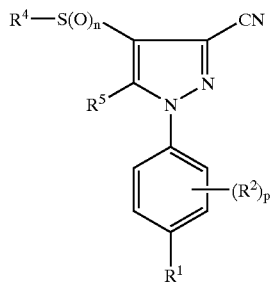

(I)

wherein:
$R^1$ is halogen, $C_1-C_4$ haloalkyl, $C_1-C_4$ haloalkoxy or $SF_5$;
$R^2$ is halogen, the various $R^2$ being the same or different and being in the 2-, the 6- or the 2,6-positions;
$R^4$ is halogen, $C_1-C_4$ alkyl or $C_1-C_4$ haloalkyl;
$R^5$ is halogen, $C_1-C_4$ alkyl or amino;
n is 0, 1 or 2; and
p is 0, 1, or 2;
in an amount of from 1 to 10% by weight of the total weight of the composition;

(b) a weakly polar solvent having a positive dipole moment greater than 1 and a solubility in water of less than 10%, in an amount of from 3 to 90% by weight of the total weight of the composition, the weakly polar solvent consisting of one or more members selected from the group consisting of N-octyl-2-pyrrolidone, N-dodecyl-2-pyrrolidone, N-dodecyl-caprolactam and a glycolic ether;

(c) an emulsifying agent selected from a mixture of polyoxyethylene styryl phenyl ether and calcium alkylbenzenesulfonate or a mixture of polyoxyethylene (castor oil) ether and calcium alkylbenzenesulfonate, in an amount of from 5 to 40% by weight of the total weight of the composition; and (d) a polar solvent having a positive dipole moment greater than 1 and a solubility in water of greater than 10%, in an amount of up to 20% by weight of the total weight of the composition, the polar solvent consisting of one or more members selected from the group consisting of N-cyclohexyl-2-pyrrolidone, caprolactone, butyrolactone, tripropyleneglycol monomethyl ether and diethyleneglycol dimethyl ether;

wherein said composition is capable of dilution with water without formation of crystals.

18. A method according to claim 17, wherein $R^1$ is halogen, halomethyl, halomethoxy or $SF_5$; $R^4$ is halogen, methyl or halomethyl; $R^5$ is halogen, methyl or amino; and p is 2.

19. A method according to claim 17, wherein the compound of formula (I) is 5-amino-3-cyano-1-(2,6-dichloro-4-trifluoromethylphenyl)-4-trifluoromethylsulfinylpyrazole.

20. A method according to claim 17, wherein the weakly polar solvent is diethylene glycol mono-2-ethylhexyl ether.

21. A method according to claim 17, wherein the amount of weakly polar solvent is from 5 to 30% by weight of the total weight of the composition.

22. A method according to claim 17, wherein the amount of compound of formula (I) applied is from 0.01 to 15 mg/m².

23. A method according to claim 17, wherein the amount of compound of formula (I) applied is from 0.1 to 5 mg/m².

24. A method for controlling termites at a locus infested thereby or expected to be infested thereby, said method comprising applying to said locus a termiticidally effective amount of an emulsifiable composition consisting essentially of:

(a) a termiticidally effective amount of a compound having the formula:

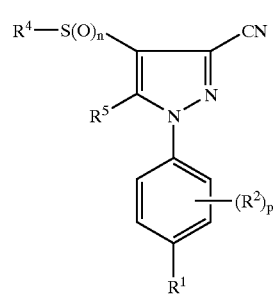

(I)

wherein:
$R^1$ is halogen, $C_1-C_4$ haloalkyl, $C_1-C_4$ haloalkoxy or $SF_5$;
$R^2$ is halogen, the various $R^2$ being the same or different and being in the 2-, the 6- or the 2,6-positions;
$R^4$ is halogen, $C_1-C_4$ alkyl or $C_1-C_4$ haloalkyl;
$R^5$ is halogen, $C_1-C_4$ alkyl or amino;
n is 0, 1 or 2; and
p is 0, 1, or 2;
in an amount of from 1 to 10% by weight of the total weight of the composition;

(b) a weakly polar solvent having a positive dipole moment greater than 1 and a solubility in water of less than 10%, in an amount of from 3 to 90% by weight of the total weight of the composition, the weakly polar solvent consisting of one or more members selected from the group consisting of N-octyl-2-pyrrolidone, N-dodecyl-2-pyrrolidone, N-dodecyl-caprolactam and a glycolic ether;

(c) an emulsifying agent selected from a mixture of polyoxyethylene styryl phenyl ether and calcium alkylbenzenesulfonate or a mixture of polyoxyethylene (castor oil) ether and calcium alkylbenzenesulfonate, in an amount of from 5 to 40% by weight of the total weight of the composition;

(d) a polar solvent having a positive dipole moment greater than 1 and a solubility in water of greater than 10%, in an amount of up to 20% by weight of the total weight of the composition, the polar solvent consisting of one or more members selected from the group consisting of N-cyclohexyl-2-pyrrolidone, caprolactone, butyrolactone, tripropyleneglycol monomethyl ether and diethyleneglycol dimethyl ether; and (e) an aromatic solvent which is in liquid state at a temperature below 30° C. or which has a boiling point of at least 200° C., in an amount of up to 90% by weight of the total weight of the composition;

wherein said composition is capable of dilution with water without formation of crystals.

25. A method according to claim 24, wherein $R^1$ is halogen, halomethyl, halomethoxy or $SF_5$; $R^4$ is halogen, methyl or halomethyl; $R^5$ is halogen, methyl or amino; and p is 2.

26. A method according to claim 24, wherein the compound of formula (I) is 5-amino-3-cyano-1-(2,6-dichloro-4-trifluoromethylphenyl)-4-trifluoromethylsulfinylpyrazole.

27. A method according to claim 24, wherein the weakly polar solvent is diethylene glycol mono-2-ethylhexyl ether.

28. A method according to claim 24, wherein the amount of weakly polar solvent is from 5 to 30% by weight of the total weight of the composition.

29. A method according to claim 24, wherein the amount of aromatic solvent is more than 50% by weight of the total weight of the composition.

30. A method according to claim 24, wherein the amount of compound of formula (I) applied is from 0.01 to 15 mg/m$^2$.

31. A method according to claim 24, wherein the amount of compound of formula (I) applied is from 0.1 to 5 mg/m$^2$.

* * * * *